United States Patent [19]

Nagai et al.

[11] 4,412,453

[45] Nov. 1, 1983

[54] METHOD FOR DETECTING BRAZING DEFECTS IN PLATE-FIN TYPE HEAT EXCHANGERS

[75] Inventors: Nobuyuki Nagai, Kobe; Eiji Takahashi, Akashi; Yoji Matsumoto, Akashi; Hideaki Ohtsu, Akashi, all of Japan

[73] Assignee: Kabushiki Kaisha Kobe Sekio Sho, Kobe, Japan

[21] Appl. No.: 311,599

[22] Filed: Oct. 15, 1981

[30] Foreign Application Priority Data

Oct. 16, 1980 [JP] Japan ................. 55-145528

[51] Int. Cl.³ .......................................... G01N 29/04
[52] U.S. Cl. ........................................ 73/601; 73/599; 378/59
[58] Field of Search ............... 73/601, 599, 600, 618, 73/582, 583, 588; 165/11 R; 378/58, 59

[56] References Cited

U.S. PATENT DOCUMENTS 3,351,760  11/1967  Brown ..................................... 378/58
3,686,932  8/1972  Ries et al. ............................. 73/601

FOREIGN PATENT DOCUMENTS 400844  4/1974  U.S.S.R. ................................... 73/588

*Primary Examiner*—Stephen A. Kreitman
*Attorney, Agent, or Firm*—Oblon, Fisher, Spivak, McClelland & Maier

[57] ABSTRACT

A method for detecting brazing defects in a plate-fin type heat exchanger with a brazed core structure having a number of wavy fin members alternately with a number of parallelly spaced plate members, in which a pulsed sound in the frequency range of several tens KHz to several hundreds KHz is transmitted across the fin and plate members from a pulser located on one outermost plate member to a sensor located on the other outermost plate member, detecting the positions and sizes of brazing defects two-dimensionally on a plane on the basis of the level of sound received by the sensor. Three-dimensional detection of the position of the defect is also possible by combining therewith a radiographic inspection using a radiant ray source which is located on one lateral side of the core structure to irradiate a radiant ray in a direction substantially parallel with the plate members of the core structure.

8 Claims, 7 Drawing Figures

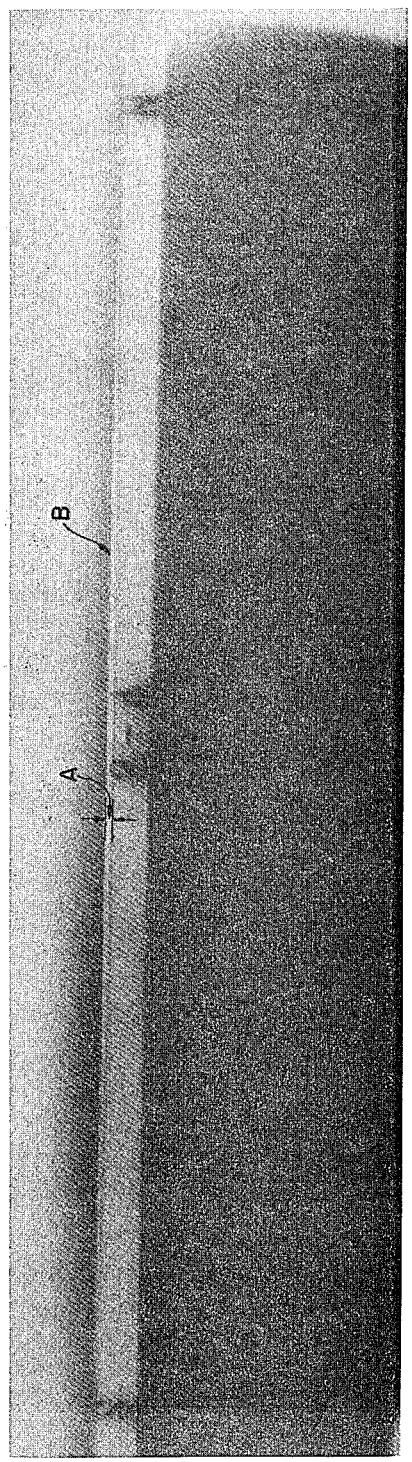

METHOD FOR DETECTING BRAZING DEFECTS IN PLATE-FIN TYPE HEAT EXCHANGERS

BACKGROUND OF THE INVENTION (1) Field of the Invention

This invention relates to a method for detecting brazing defect in plate-fin type heat exchangers with aluminum-brazed plates and fins.

(2) Description of the Prior Art

Plate-fin type heat exchangers include the so-called core structure which has wavy fin member alternately between a number of parallely spaced plate members of aluminum, stainless steel or the like, the contacting joint portions of the fin and plate members being brazed to each other by immersing the core assembly in a hot salt bath. Therefore, in the production of a large-sized plate-fin type heat exchanger, for example, there sometimes occurs a problem in that the brazing of the joint portions of the wavy fins is obstructed over certain areas by air which remains in the core assembly even after immersion in the salt bath.

Such brazing defects in the heat exchanger give rise to a serious problem in that the heat exchanger is ruptured from the defective portions in the subsequent pressure endurance test or during use under high pressure conditions. In this connection, it has not been contemplated or proposed to provide a simple and reliable mechanism for detecting the unbrazed portions, in view of the complicated construction of the plate-fin type heat exchanger. With ordinary steel materials such as steel plates, steel pipes and steel rods, ultrasonic flaw detectors operating with ultrasonic waves of frequencies over several thousands KHz are widely used for internal flaw detection. For detecting internal flaws in such solid materials, the ultrasonic wave to be applied is required to have high directionability and therefore normally is in a high frequency range of 2 M to 5 M. However, in a case where the ultrasonic wave of the high frequency range is applied to a plate-fin type heat exchanger, a marked attenuation of the ultrasonic wave occurs due to its reflections in the cavities of the fluid or gas passages formed in the heat exchanger and as a result such fails to detect the brazing defect. Therefore, the conventional ultrasonic flaw detectors have been unsuitable for or incapable of detecting brazing failures in the plate-fin type heat exchangers containing the fluid passages defined by the plate and fin members.

SUMMARY OF THE INVENTION

In view of the above-mentioned circumstances, the present inventors conducted as intensive study and achieved the present invention on the basis of the finding that a pulsed sound of a low frequency which is unsuitable for the ultrasonic flaw detection well permeates the core of the plate-fin type heat exchanger when applied across the overlapped plate and fin members of the core structure in spite of the existence of a large number of cavities formed by the fluid or gas passages of the core, permitting detection of the brazing failures or other defects two-dimensionally on a plane of a plate or three-dimensionally by combined use of a radiographic inspection.

According to one feature of the present invention, there is provided a method for detecting defects in a plate-fin type heat exchanger including a core structure having a number of wavy fin members alternately positional with parallely spaced plate members, the fin members being brazed to the plate members at the respective contacting portions, the method being characterized by the step of directing across the fin and plate members a pulsed sound from a pulser located on an outermost plate member toward a sensor oppposingly located on the other outermost plate member, and detecting the positions and sizes of unbrazed or defective portions two-dimensionally on a plane of a plate on the basis of the level of passed pulsed sound received by the sensor.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein:

FIGS. 3 to 6 are diagrams of passed sound in the inspection by the method of the invention, of which FIGS. 3 and 4 show the shape of passed sound in internal portions of a defect;

FIG. 5 shows the shape of a sound portion;

FIG. 6 shows the shape at a marginal portion of a defect; and

FIG. 7 is a radigraphic image obtained by the method of the present invention.

DETAILED DESCRIPTION OF THE PREFERRED EMBODIMENTS

Figure 1:
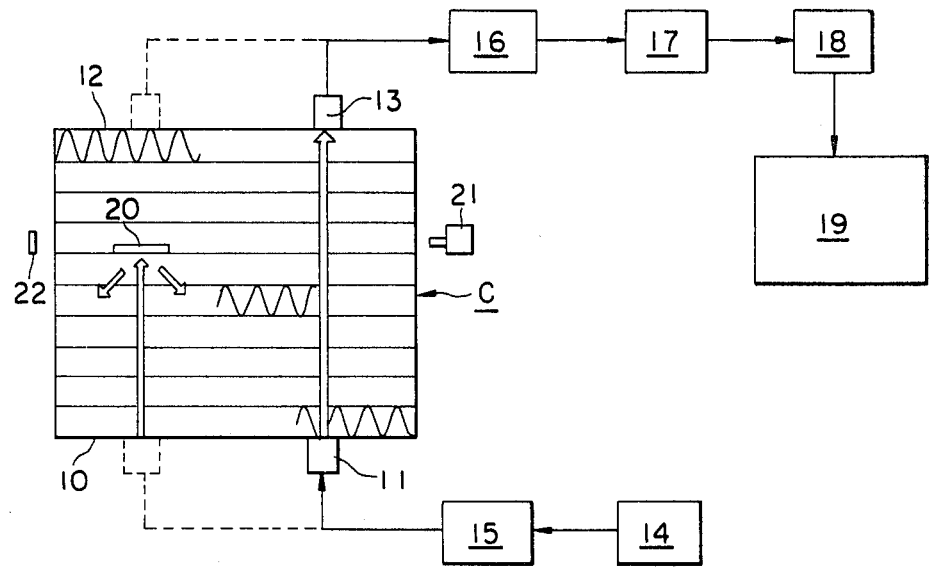
FIG. 1 is a block diagram illustrating the inspection method according to the present invention.

Referring to the block diagram of FIG. 1 which illustrates the method of the invention, a pulser 11 is positioned on one outermost plate member 10 of a brazed core structure C and a sensor 13 is positioned on the other outermost plate member 12 in vis-a-vis relation with the pulser as shown. The pulser 11 is moved sequentially along box or other marks which are provided on the outermost plate 10 to indicate the inspection points or areas, also moving the sensor in synchronism therewith along similar box marks which are provided on the other outermost plate 12. Of course, it is preferred that the box marks are provided at positions which coincide with the brazed portions of the alternately overlapped plates and fins. The pulser 11 and sensor 13 may be moved manually or may be moved automatically through a suitable interlocking mechanism in such a manner as to scan the box marks corresponding to the brazed portions of the core structure.

The synchronized sound pulses which are produced by a pulse generator 15 under control of a pulse synchronizer 14 are sent forth by the pulser across the multi-layered structure of the core, the sensor receiving the sound which is transmitted across the core. The transmitted sound or the sound received by the sensor is sent through a preamplifier 16 and a filter 17 and amplified at a main amplifier 18 before it is displayed on an oscilloscope 19 in the same manner as in the ultrasonic flaw detection.

The pulsed sound used in the present invention is in a frequency range of from several tens KHz to several hundreds KHz, which is quite different from the frequency range of the pulsed sound employed in the conventional ultrasonic flaw detection. If the frequency is smaller than several tens KHz, the pulsed sound is propagated around an unbrazed or defective portion of the heat exchanger, if any, and thus the inspection results in unacceptably low accuracy. On the other hand, with a frequency over one thousand KHz, it becomes difficult to transmit the sound effectively due to considerable sound attenuation across the core and increased sound reflections as mentioned hereinbefore.

The optimum range of the inspecting frequency varies depending upon the exciting voltage of the sensor, for example, it is preferred to be 30–400 KHz in a case where the exciting voltage of the sensor is lower than 100 V. The output signal form is displayed on the oscilloscope, indicating on the ordinate the level of the passed sound by way of voltage in relation with time on the abscissa. Therefore, if a plate-fin type heat exchanger contains a defect like an unbrazed portion, the pulse sound is reflected at the defect and the level of the passed pulse sound is lowered, permitting spotting of the defect as shown in the drawings. Namely, the positions and sizes of the defects can be reproduced two-dimensionally on a plane simply by scanning along the outermost plates of the core with the pulser and sensor which are opposingly positioned across the core structure.

In addition to the above-described method, the radiant ray inspection which will be described hereinafter may be employed under particular conditions for three-dimensional detection of the brazing failures in the plate-fin type heat exchangers. More specifically, radiant rays are directed parallel with the multilayered plate members to find brazing failures by way the resulting film image of the passed ray. In this instance, it is especially important to position the radiant ray source substantially at a median point between two adjacent plate members so that the beam is passed substantially parallel to the plate members. In this manner, the radiant ray source is moved sequentially to median points of the succeeding plate members to obtain the corresponding film images. This contributes to enhancement of the accuracy of the detection of brazing failures to a significant degree. However, the accuracy of detection is lowered when the source of the radiant ray is deviated from the median point of the adjacent plates or when the radiant beam is not passed parallel with the plate members.

According to the present invention, the ultrasonic inspection detects brazing failures in a direction perpendicular to the respective plate members while the radiant ray inspection detects brazing failures in a direction parallel with the plate members. It follows that the positions of the brazing defects can be three-dimensionally spotted by the combination of the ultrasonic and radiant ray inspections. In this instance, it is preferred to detect in the first place the position of a brazing defect on a plane of the plate by the ultrasonic inspection. In the radiant ray inspection which follows the ultrasonic inspection, the radiant ray source is preferred to be located on a side remote from the spotted brazing defect. Thus, the position of the brazing defect can be detected three-dimensionally and in a reliable manner by the combination of the ultrasonic and radiant ray inspections.

Figure 2:
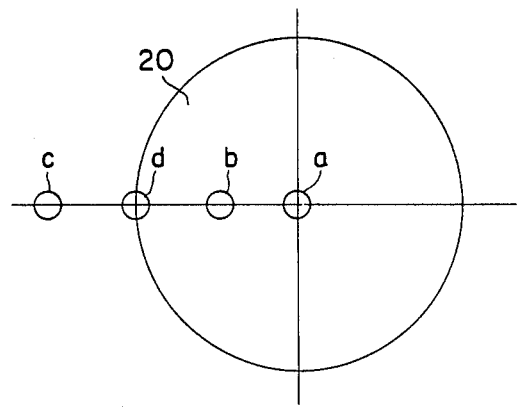
FIG. 2 is a diagrammatic view showing a preformed brazing defect and inspecting positions.
Figure 3:
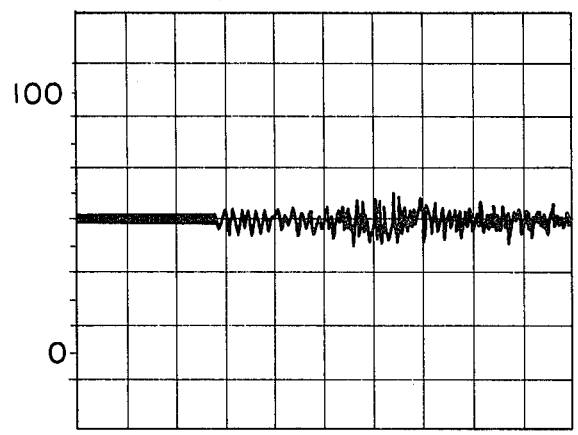
Figure 4:
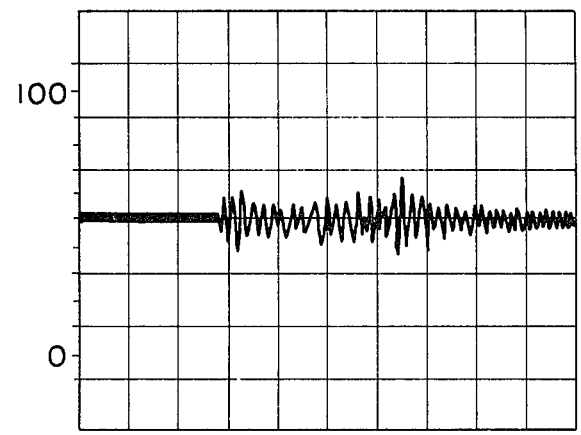
Figure 5:
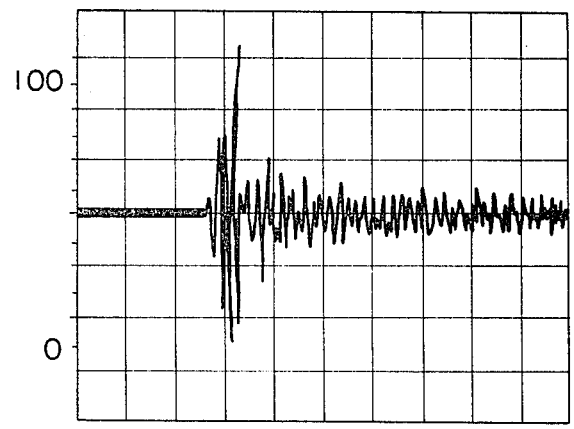
Figure 6:
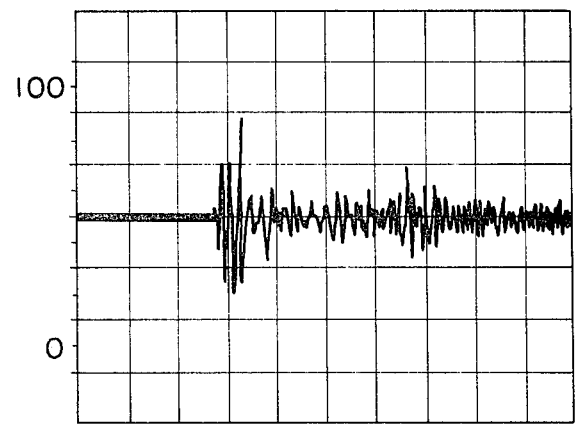

Hereafter, the invention is illustrated more particularly by way of an example. Aluminum plates of 1250 mm (l) $\times$ 1000 mm (w) $\times$ 0.8 mm (t) and wavy fins of 0.2 mm (t) $\times$ 1.4 mm (pitch) $\times$ 9.5 mm (h) were alternately stacked to form a core of 97 layers (height: 1008.3 mm), purposely forming a brazing defect of 100 mm in diameter in the plate-fin unit of the 48th layer when brazing the core in a salt bath. A pulser and a sensor were positioned vis-a-vis on the opposite outermost plate members of the core, sending pulsed sound of 140 KHz from the pulser to the sensor. The passed pulsed sound level was monitored by an oscilloscope with a gain of 77 dB. FIG. 2 shows the defect 20 and inspected positions. The position (a) is located at the center of the defect, and the inspected position (b) is located also within the range of the defect although not at the center thereof. The shapes of passed sound signals at the positions (a) and (b) are shown in FIGS. 3 and 4, respectively. In these diagrams, the passed sound level is indicated by voltage on the ordinate (scale unit: 1 volt) in relation with time (scale unit: 0.1 millisecond). It is seen that the passed sound level is markedly lowered at the defective portion due to increased sound reflections thereat. At the inspected position (c) which was located at a distance of 30 mm from the marginal edge of the defect, the level of the passed sound is clearly increased as shown in FIG. 5. Further, at the inspected position (d) which was located at the marginal edge of the defect, the passed sound takes an intermediate shape between the sound shapes at the defective and sound portions owing to detouring propagation in part of the transmitted sound as shown in FIG. 6.

Thereafter, X-ray of 250 kVp or $\gamma$ ray was irradiated from a radiant ray source 21 which was positioned at the median point between plate members and on the side remote from the brazing defect. FIG. 7 shows the resulting X-ray image, in which the reference character B denotes the image of the brazed portion along a plate and the reference character A indicates a brazing defect appearing as a variation in tone.

It will be understood from the foregoing description that, according to the method of the present invention, the positions and sizes of brazing defects in a plate-fin type heat exchanger which contains a large number of cavities as passages of a fluid or gas can be two-dimensionally detected on a plane of a plate in a simple and reliable manner by the use of pulsed sound in the frequency range of several tens KHz to several hundreds KHz which are not used in the conventional ultrasonic flaw detection. Further, it has become possible to three-dimensional detect the defects simply by effecting radiographic inspection in a direction parallel with the plate members in consideration of the two-dimensionally detected positions and sizes of the defects. Thus, the method of the invention permits spotting of the brazing defects in an efficient and economical manner without requiring scanning of all sides of the core structure.

What is claimed is:

1. A method for detecting brazing defects in a plate-fin type heat exchanger utilizing a pulser and a sensor and including a brazed core structure having a number of wavy-like fin members positioned alternately with a number of parallelly spaced plate members, with comprises:

directing a pulsed sound across said fin and said plate members in a frequency range of from several tens KHz to several hundreds KHz from said pulser located on one outermost plate member to said sensor located opposingly on the other outermost plate member; and two-dimensionally detecting the position and size of a brazing defect on a plane of a plate on the basis of the level of the sound received by said sensor.

2. The method of claim 1, which further comprises moving said pulser and sensor along said outermost plate members simultaneously and continuously while maintaining vis-a-vis positions across said core structure.

3. The method of claim 1, which further comprises transmitting a pulsed sound in the frequency range of 30–400 KHz when the exciting voltage of said sensor is lower than 100 V.

4. A method for detecting brazing defects in a plate-fin type heat exchanger utilizing a pulser, a sensor and a radiant ray source including a brazed core structure having a plurality of wavy-like fin members alternately positioned between a number of parallelly spaced plate members, which comprises:

directing a pulsed sound across said fin and plate members in a frequency range of from several tens KHz to several hundreds KHz from said sensor located opposingly on the other outermost plate member;

two dimensionally detecting the position and size of a brazing defect on a plane on the basis of the level of the sound received by said sensor;

irradiating an radiant ray in a direction substantially parallel with said plate members from said radiant ray source located substantially at a median point between two adjacent plate members on one lateral side of said core structure; and three-dimensionally detecting the position of said brazing defect.

5. The method of claim 4, wherein said irradiating of radiant ray further comprising irradiating an X-ray.

6. A method of claim 4, wherein said irradiating of a radiant ray further comprises irradiating a $\gamma$-ray.

7. A method for detecting brazing defects in a plate-fin type heat exchanger utilizing a radiosensitive film and a radiant ray source and including a brazed core structure having a plurality of wavy-like fin members alternately positioned with a number of parallelly spaced plate members, which comprises:

irradiating a radiant ray in a direction substantially parallel with said plate members from said radiant ray source located substantially at a median point between two adjacent plate members on one lateral side of said core structure toward said radiosensitive film located on the opposite lateral side of said core structure; and successively shifting said radiant ray source to a median point of next two adjacent plate members to two-dimensionally detect the positions of brazing defects on a plane perpendicular to said plate members.

8. The method of claim 4 or 7, wherein said radiant ray source is located on a side remote from a brazing defect.

* * * * *